(12) United States Patent
King et al.

(10) Patent No.: US 6,423,268 B1
(45) Date of Patent: Jul. 23, 2002

(54) BLOOD HEATING SYSTEM WITH MUTUALLY EXCLUSIVE RELAY-CONTROLLED HEAT EXCHANGERS

(75) Inventors: Luther M. King, P.O. Box 669, 114 Main St., Grapeland, TX (US) 75844; Douglas E. Platt, Grapeland, TX (US)

(73) Assignee: Luther M. King, Grapeland, TX (US)

( * ) Notice: Subject to any disclaimer, the term of this patent is extended or adjusted under 35 U.S.C. 154(b) by 0 days.

(21) Appl. No.: 09/760,429

(22) Filed: Jan. 16, 2001

(51) Int. Cl.[7] .................. A61M 1/36; A61M 37/00; B01D 37/02; C02F 9/00; F25B 29/00
(52) U.S. Cl. .................. 422/44; 422/46; 210/195.1; 210/260; 604/6.13; 604/113; 165/261
(58) Field of Search .................. 210/177, 181, 210/182, 195.1, 195.2, 258, 260; 604/113, 6.13; 165/261; 422/44–46; 337/14

(56) References Cited

U.S. PATENT DOCUMENTS

| | | | |
|---|---|---|---|
| 3,724,536 A | * | 4/1973 | Baxter .................. 165/185 |
| 4,729,424 A | * | 3/1988 | Mizuno et al. ............. 165/261 |
| 5,120,501 A | | 6/1992 | Mathewson et al. |
| 5,385,540 A | * | 1/1995 | Abbott et al. .................. 604/4 |
| 5,403,281 A | | 4/1995 | O'Neill et al. |
| 5,891,330 A | * | 4/1999 | Morris .................. 210/104 |
| 6,180,000 B1 | * | 1/2001 | Wilbur et al. .............. 210/143 |

* cited by examiner

Primary Examiner—Angela D. Sykes
Assistant Examiner—Leslie Deak
(74) Attorney, Agent, or Firm—Harrison & Egbert

(57) ABSTRACT

A blood heating system for use in open heart surgery including an arterial/venous fluid circuit, a cardioplegia fluid circuit independent of the arterial/venous fluid circuit, a first heater in heat exchange relationship with the arterial/venous fluid circuit, a second heater in heat exchange relationship with the cardioplegia fluid circuit, a power supply connected to the first and second heaters so as to supply a desired electrical power, to the first and second heaters, and a controller electrically interconnected to the power supply and to the first and second heaters such that the first and second heaters cannot be activated simultaneously. A relay is electrically interconnected between the first and second heaters and the power supply so as to deactivate one of the heaters when the other of the heaters is activated. A timer is connected to the relay so as to alternately activate and deactivate the respective heaters after a desired period of time.

18 Claims, 4 Drawing Sheets

BLOOD HEATING SYSTEM WITH MUTUALLY EXCLUSIVE RELAY-CONTROLLED HEAT EXCHANGERS

BACKGROUND OF THE INVENTION

1. Field of the Invention

The present invention relates to heat exchange systems used for open heart surgery. More particularly, the present invention relates to systems used for the cooling, heating and recirculating of fluids associated with arterial/venous and cardioplegia fluid lines in cardiovascular surgery.

2. Description of Invention

Typically, a circulatory support and cardioplegia administration system includes (among other things) a venous catheter for draining blood from the patient's venous system, a venous line for transferring blood drained with the venous catheter to a venous reservoir, a heat exchanger and an oxygenator connected via a transfer line to the outlet of the venous reservoir, and an arterial line connected to the outlet of the oxygenator to supply the oxygenated blood to a cannula, which returns the blood to the patient's heart. Such systems have included other components or subsystems as well. One such subsystem relates to blood recovery from the surgical site (e.g., the pericardial sac) and that system would include a number of blood suction devices (intracardiac suckers) that supply blood to the cardiotomy reservoir that collects, defoarns and filters the recovered blood before supplying it to the venous reservoir of the main system.

Another subsystem is the cardioplegia administration system. Cardioplegia is a commonly used technique for protecting the heart during heart surgery. Typically, cooled cardioplegia solution (e.g., a potassium solution, cooled blood or a blood/potassium solution) is administered to the patient's heart in either the antegrade or retrograde direction through either the patient's aorta or coronary sinus, respectively. "Antegrade" refers to the direction of normal blood flow, and "retrograde" refers to the direction opposite of normal blood flow.

The cardioplegia solution stops the heart and reduces its temperature to minimize damage to the heart during surgery. Such cardioplegia solutions are typically introduced into the heart in an intermittent fashion. For example, a bolus of cooled cardioplegia solution may be delivered to the heart to initially arrest the heart, and then the subsequent doses of the cardioplegia solution may be administered approximately every 15–20 minutes.

Cardioplegia subsystems have included a heat exchanger connected to a source of cardioplegia solution and/or blood, a bubble trap to collect air emboli to prevent supplying such emboli to the patient, a temperature monitor for measuring and displaying the temperature of the cardioplegia solution downstream of the heat exchanger, a cardioplegia supply line connected to the outlet of the bubble trap/temperature monitor, and a catheter connected to the downstream end of the cardioplegia supply line for supplying the cardioplegia solution to the heart.

In the past, separate systems have been used for the heating and cooling of the arterial supply line and the heating and cooling of the cardioplegia supply line. Since the arterial supply line and the cardioplegia supply line are separate and independent circuits, independent systems have often been used for the heating and cooling of the fluids within such supply lines. Unfortunately, the use of separate heating and cooling systems occupies a great deal of space within the operating room. The footprint within the operating room is extremely limited. As a result, additional heating and cooling systems can occupy an excessive amount of space. Each of the separate heating and cooling systems requires its own cooling or ice bath. Additionally, each of these heating and cooling systems will require separate heating facilities.

Very importantly, each of the heating and cooling systems will utilize separate 1500 watt heaters. Each of these 1500 watt heaters will draw approximately sixteen amps worth of power. When each of the heaters is on simultaneously, the power draw will be approximately thirty amps. This will be in excess of the twenty amp power supply which would be available for such heaters. As a result, in the open heart surgery operating environment, when both of the heaters for the separate systems are activated, circuit breakers will trip and cause the systems to shut down. As such, it is very important to avoid the excessive draw of amperage from the power supply. Furthermore, when both of the systems are activated at the same time, a spike of current can occur which can damage other equipment within the operating room environment. So as to maintain the integrity and reliability of the other equipment in the operating room environment, it is very important to avoid power surges or current spikes.

It is an object of the present invention to provide a fluid heating system which avoids unnecessary power surges, spikes, and current draw.

It is another object of the present invention to provide a heating system for use in open heart surgery which does not require separate systems for the heating and cooling of the separate fluid lines.

It is a further object of the present invention to provide a heating system for use in open heart surgery which can be operated from a single power outlet.

It is a further object of the present invention to provide a heating system for use in open heart surgery which minimizes space usage in the operating room environment.

It is still a further object of the present invention to provide a heating system for use in open heart surgery which prevents the simultaneous operation of the separate heaters.

These and other objects and advantages of the present invention will become apparent from a reading of the attached specification and appended claims.

SUMMARY OF THE INVENTION

The present invention is a blood heating system for use in open heart surgery comprising a first fluid circuit, a second fluid circuit defining a fluid flow path independent of the first fluid circuit, a first heater in heat exchange relationship with the first fluid circuit, a second heater in heat exchange relationship with the second fluid circuit, a power supply connected to the first and second heaters so as to supply a desired electrical power to the first and second heaters, and a controller electrically connected to the power supply and to the first and second heaters such that the first and second heaters cannot be activated simultaneously.

In the system of the present invention, each of the first and second heaters are of a type that draw between 15 and 20 amps of electrical energy from the power supply. The controller is a relay which is interconnected between the heaters and the power supply. The relay serves to deactivate one of the heaters when the other of the heaters is activated. A timer can be connected to the relay so as to activate and deactivate each of the heaters after a desired period of time such that each of the heaters will heat alternately. The timer will activate the first heater when the first heater is deactivated and activate the second heater after the first heater is deactivated. The timer will serve to activate and deactivate the respective heaters after a desired period of time (e.g. four seconds).

In the present invention, the power supply is a single 110 volt source of electrical energy providing twenty amps of power. The relay serves to energize one of the heaters as the other of the heaters is de-energized. The relay includes a first solid state relay interposed between the power supply in the first heater. The first solid state relay can be switched by the controller so as to pass AC power from the power supply to the first heater. A second solid state relay is interposed between the power supply and the second heater. The second solid state relay is switched by the controller so as to pass AC power from the power supply to the second heater. The power supply is from a single electrical outlet.

The controller of the present invention can further include a first sensor which is interactive with the first fluid circuit so as to sense a temperature of a fluid within the first fluid circuit. The first sensor is electrically connected to the first solid state relay so as to activate the first heater when the temperature of the fluid in the first fluid circuit is below a desired level. A second sensor is interactive with the second fluid circuit so as to sense the temperature of a fluid in the second fluid circuit. The second sensor is electrically connected to the second solid state relay so as to activate the second heater when the temperature of the fluid within the second fluid circuit is below a desired level. A DC power supply can be connected to the first and second heaters so as to supply electrical energy to the first and second solid state relays so as to switch the respective relays. The first sensor can deactivate the first heater when the temperature of the fluid is above a desired level. The second sensor can deactivate the second heater when the temperature of the fluid is above a desired level.

The present invention is also a method of heating fluid circuits used in open heart surgery. This method includes the steps of: (1) connecting a first heater in heat exchange relationship to the first fluid circuit; (2) connecting a second heater in heat exchange relationship with the second fluid circuit; (3) supplying electrical energy to the first and second heaters from a single power supply; and (4) deactivating one of the first and second heaters when the other of the first and second heaters is activated such that the heaters cannot be activated simultaneously. This step of deactivating includes switching one of the heaters to an active state as the other of the heaters is deactivated. Power is supplied to the first and second heaters such that the first and second heaters never draw cumulatively more than 20 amps of power from the single power supply. A first relay is connected to the first heater. A second relay is connected to the second heater. The first relay activates the first heater when the second relay deactivates the second heater. The step of switching can include the use of a timer which alternates the first and second heaters between the active state and the deactive state for a desired period of time.

DETAILED DESCRIPTION OF THE PRESENT INVENTION

Figure 1:
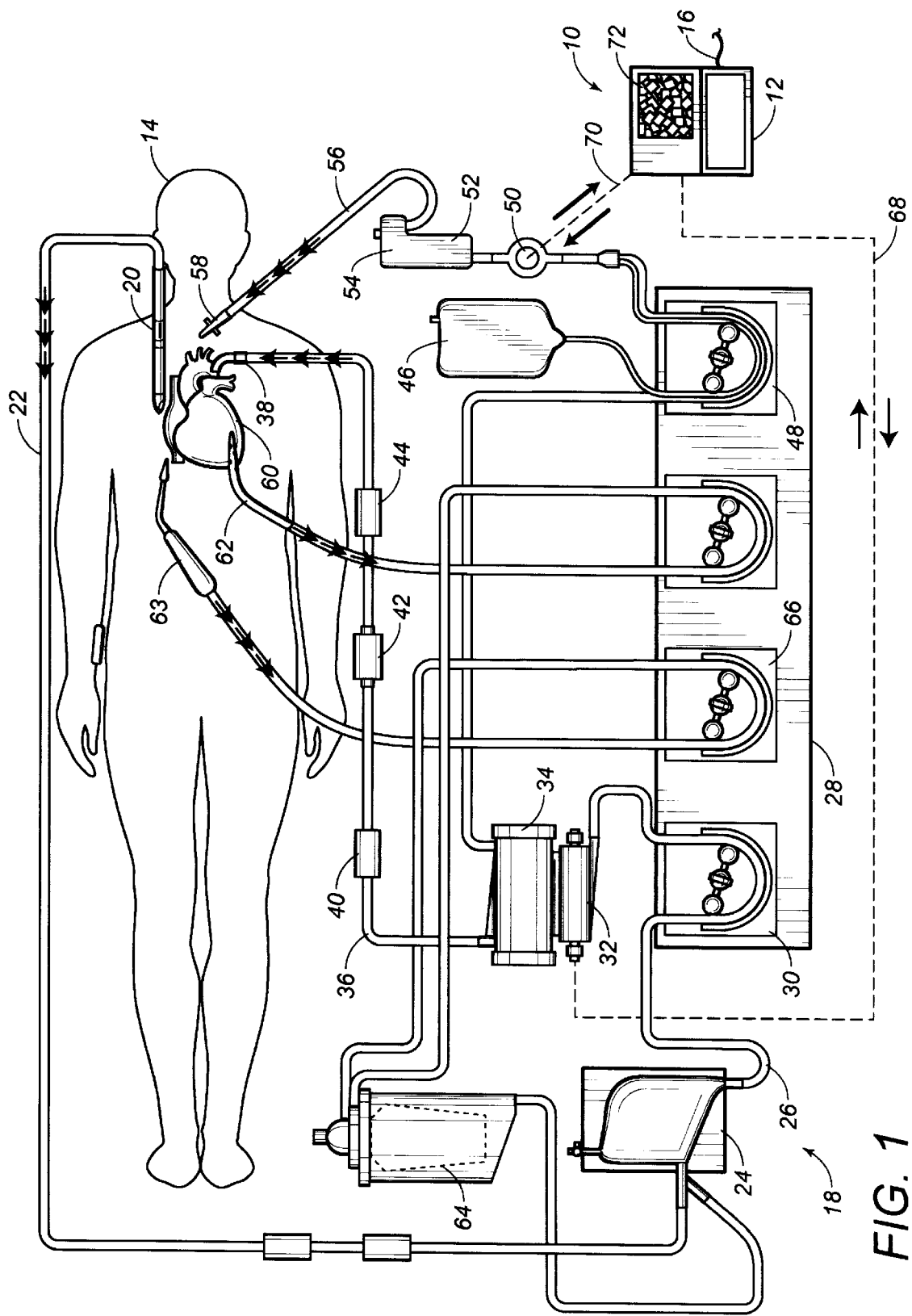
FIG. 1 is a diagrammatic illustration of the present invention as used in open heart surgery.

Referring to FIG. 1, there is shown at 10 the system of the present invention for carrying out open heart surgery. The system 10 includes a temperature control and monitor system 12 which is used for the heating and cooling of separate fluid flow lines during the open heart surgery associated with patient 14. It can be seen that the present invention is the use of a single unit for the heating and cooling of the separate fluid flow lines. The temperature control and monitor system 12 is powered along a single power supply line 16.

In FIG. 1, there is shown the standard circulatory support and cardioplegia administration system 18 as used in open heart surgery. This system includes a venous catheter 20 for draining blood from the patient's venous system. A venous line 22 is connected to the venous catheter 20 for transferring blood drained by the venous catheter to a venous reservoir 24. A line 26 passes the blood from the venous reservoir 24 to a heart-lung machine 28. The blood from line 26 passes to a peristaltic pump 30. Peristaltic pump 30 will simulate the action of the heart in delivering fluids to the venous system of the patient 14. The pump 30 passes the blood outwardly therefrom into a heat exchanger 32 and to an oxygenator 34. The heat exchanger 32 and the oxygenator 34 are connected, through the pump 30, to the outlet of the venous reservoir 24. An arterial line 36 is connected to the outlet of the oxygenator 34 so as to supply the oxygenated blood to an arterial cannula 38. Various filters and detectors 40, 42 and 44 can serve to filter and detect bubbles associated with the blood passing from the oxygenator 34 to the arterial catheter 38.

The cardioplegia solution 46 is mixed with the blood passing through cardioplegia pump 48. A heat exchanger 50 is connected to the source of the cardioplegia solution and/or blood 46. A bubble trap 52 can collect air emboli so as to prevent supplying such emboli to the patient. A temperature monitor 54 monitors and displays the temperature of the cardioplegia solution downstream of the heat exchanger 50. A cardioplegia supply line 56 is connected to the outlet of the bubble trap 52/temperature monitor 54. A cardioplegia cannula 58 is connected to the downstream end of the cardioplegia supply line 56 for supplying the cardioplegia solution to the heart 60. A vent catheter 62 is connected to the heart 60 so as to drain the cardioplegia solution in blood from the heart 60 back to the heart-lung machine 28. Similarly, a sucker 63 can be used in association with heart 60 so as to supply blood and fluids to a cardiotomy reservoir 64 through the use of suction pump 66 in the heart-lung machine 28. The cardiotomy reservoir 64 will collect, defoam and filter the recovered blood before supplying it to the venous reservoir 24 of the main system.

It is important to note in FIG. 1 that two separate heat exchangers 32 and 50 are employed in the surgical system 18. One of the heat exchangers 32 acts directly on the loop associated with the venous and arterial lines. The other heat exchanger 50 is associated with the delivery of the cardioplegia solution directly to the heart. In the past, the heating and cooling of each of the heat exchangers 32 and 50 has been carried out by separate devices. Each of the heat exchangers 32 and 50 require a 1500 watt heater. When this 1500 watt heater is connected to a power supply, each of the heaters draws between 15 and 20 amps of power from the power supply used for the surgical procedure. Additionally, each of the devices used for the heating and cooling is a relatively large device which occupies a great deal of space in the operating room environment. The present invention avoids the problems associated with the prior art by using a single temperature control and monitor system 12 suitable for connection to a single electrical outlet through cord 16. In FIG. 1, it can be seen that the temperature control and monitor system 12 is connected by line 68 to the heat exchanger 32. Similarly, the temperature control and monitor system 12 is connected by line 70 to the heat exchanger 50. A single fluid cooling chamber 72 exists within the temperature control and monitor system 12. As a result, the present invention utilizes a single ice/water reservoir instead of the separate reservoirs used with prior systems.

Figure 2:
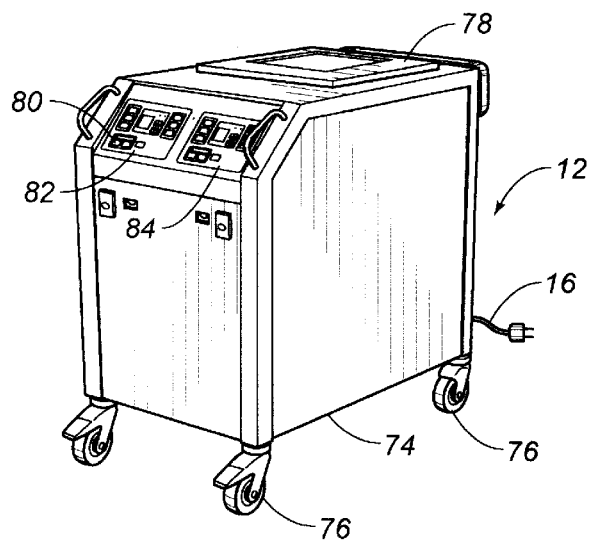
FIG. 2 is a perspective view of the controller unit as used in association with the present invention.

FIG. 2 is a perspective view showing the temperature control and monitor system 12 associated with the present invention. It can be seen that the system 12 has a housing 74 supported on wheels 76. The ice bath is located under cover 78. A single electrical cord 16 will extend outwardly of the housing 74 so as to allow the system 12 to be connected to a single source of electrical energy. A control panel 80 is positioned on the front face of the housing 74. A more detailed illustration of the control panel 80 will be shown in association with FIG. 4. The control panel 80 includes a panel 82 for the first heating/cooling system and a second panel 84 for the second heating/cooling system.

Figure 3:
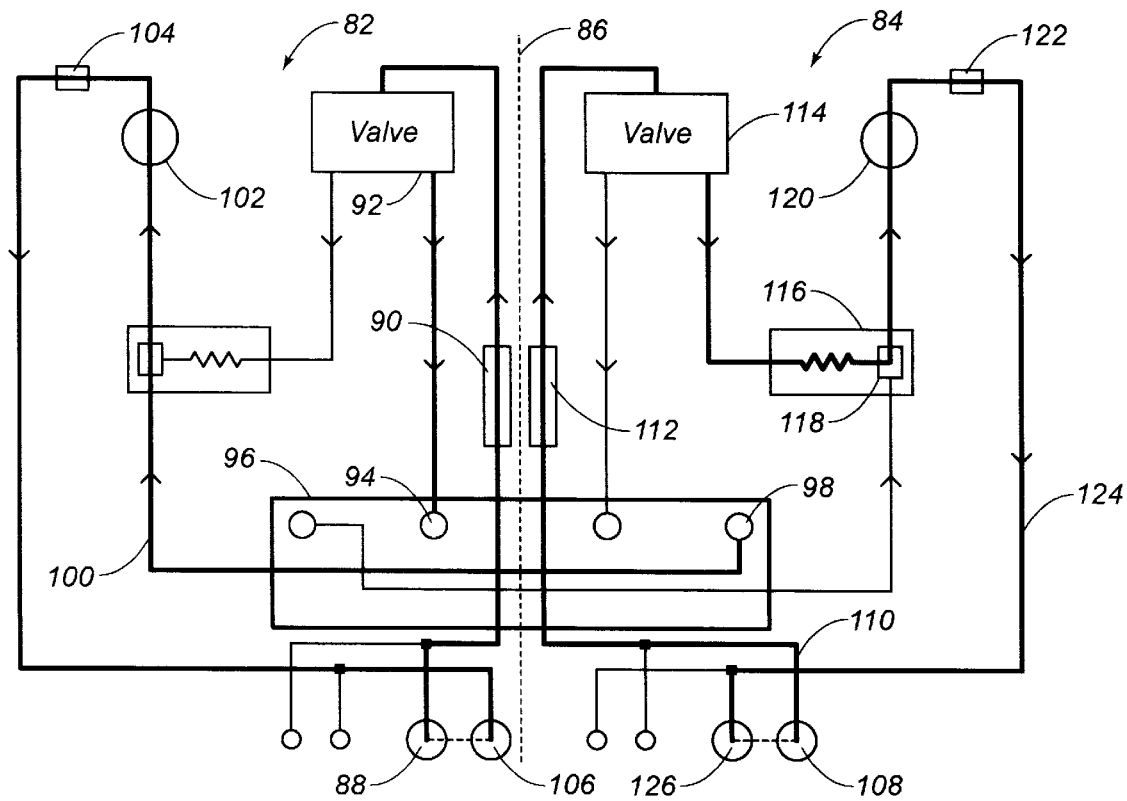
FIG. 3 is a block diagram showing the operation of the system of the present invention for the heating and cooling of the blood.

FIG. 3 shows the operation of the system of the present invention in block diagram form. Imaginary line 86 will separate the first system 82 from the second system 84 for the purposes of illustration. The first system 82 is illustrated as in the cooling mode. The second system 84 is illustrated as in the heating/recirculating mode. The temperature for each system is set independently between 0° C. and 42° C. in tenths of a degree increments (0.1° C.). The system will maintain the water output temperature at the set point at ±0.5° C. by oscillating between the cool/heat or recirculation modes.

In cooling, as shown by the first system 82, the cooling water (used in heat exchange relationship with the venous/arterial fluid line) will enter through inlet 88 and pass along the direction of the bold line shown in FIG. 3. The cooling water will pass through a strainer 90 and then pass into a valve 92 set to a position for directing the fluid to the inlet 94 of an ice bath 96. After a desired period of time within the ice bath, the cooled liquid will exit the ice bath through outlet 94 and pass along line 100 through the action of a pump 102. A main temperature sensor 104 will assure that the proper temperature of the cooling liquid is obtained. The cooled liquid will then pass outwardly of the system 82 through outlet 106. The valve 92 is a three-way valve for each of the systems 82 and 84. The ice bath 96 is capable of holding eleven gallons of an ice and water mixture. The transfer of energy from the water to the ice provides a rapid temperature decrease in the water.

The heating mode is illustrated as used in the second system 84. In this second system, the heat exchange liquid will enter through inlet 108, pass along line 110 through strainer 112 and into valve 114. As shown in FIG. 3, in association with the second system 84, the valve 114 will then be set to a position whereby the heat exchange liquid will be directed toward the heater 116. Heater 116 will heat the heat exchange liquid to a desired level. An overlimit sensor 118 is provided so as to control the heat imparted by the heater 116. Pump 120 will draw the liquid through the heater 116 and outwardly therefrom the temperature sensor 122. The heated heat exchange liquid can then pass along line 124 outwardly of the system through outlet 126.

As can be seen, each of the systems 82 and 84 is identical. As such, each of the systems 82 and 84 can be used for the heating and cooling of the heat exchange liquids used and associated with the separate fluid lines in the surgical procedures. The use of the three-way valves 92 and 114 facilitates the ability to properly route the fluids for either heating or cooling.

Figure 4:
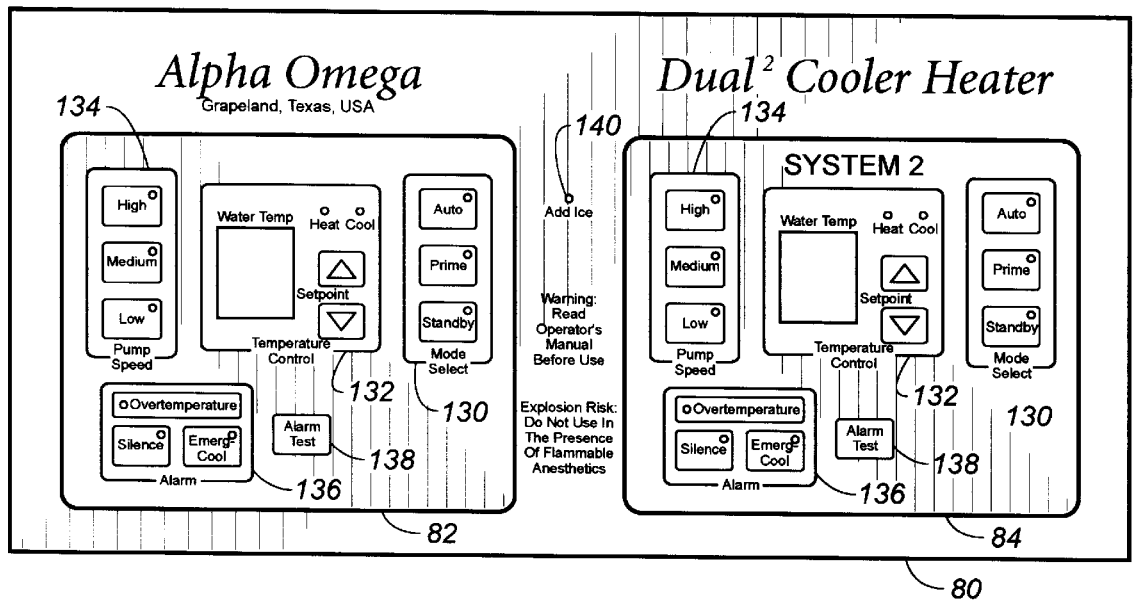
FIG. 4 is a detailed view of the control panel as provided on the unit shown in FIG. 2.

FIG. 4 shows a detailed view of the control panel 80 as used in association with the temperature control and monitor unit 12 of the present invention. It can be seen that the panel 80 includes a first system control panel 82 and a second system control panel 84. Each of the control panels 82 and 84 has an identical configuration. Individual power switches can be used so as to allow the operator to energize each of the systems 82 and 84 separately. The power switches can also provide over-current protection to their respective systems. Each of the systems 82 and 84 is equipped with an hour meter to record actual usage time. The meters record time only when their respective power switches are on.

It can be seen that each of the systems 82 and 84 includes a mode select section 130. The mode select section 130 includes a standby position in which the temperature display is active and the desired temperature can be set. The cool and heat outputs are disabled to prevent activation of the valves over extended periods or heater turn-on without water flow. The pump speed is selectable but the pump is not activated. The alarm function is active so as to allow the system to monitor water temperature. In the prime position, the pump motor is activated at the operator selected speed and the valve is toggled on and off at approximately three second intervals. This allows the water system to clear air from the internal lines. In the auto position, each system heats or cools the circulating water to match the operator-selected set point temperature. The systems automatically alternate between heating, cooling and water recirculation to maintain desired setpoint temperatures.

Each of the systems 82 and 84 includes a temperature control section 132. The temperature control section shows water temperature as it exits the pump. It also displays the setpoint temperature for the operator-selected water temperature setpoint. The "setpoint up" display allows the operator to adjust the setpoint temperature higher. The "setpoint down" indicator allows the operator to adjust the setpoint temperature lower.

Each of the systems 82 and 84 includes a pump speed section 134. The pump speed section allows the pump speed to be set at either low, medium or high. The alarm section 136 can provide an over temperature alarm if the water temperature in the system reaches 42.5° C. This alarm will reset the system to standby and deactivate the pump. The emergency cool alarm allows the operator to activate the pump and the valve so as to place the system in the cooling mode. The silence alarm will disable the alarm speaker. The alarm test display 138 will simulate an "over temperature" alarm condition in the system. An "add ice" LED 140 provides an indication to the operator that the system is attempting to cool but there is not adequate ice or cold water in the cooling tank. This provides the operator with an indication that additional ice is required in the reservoir.

Figure 6:
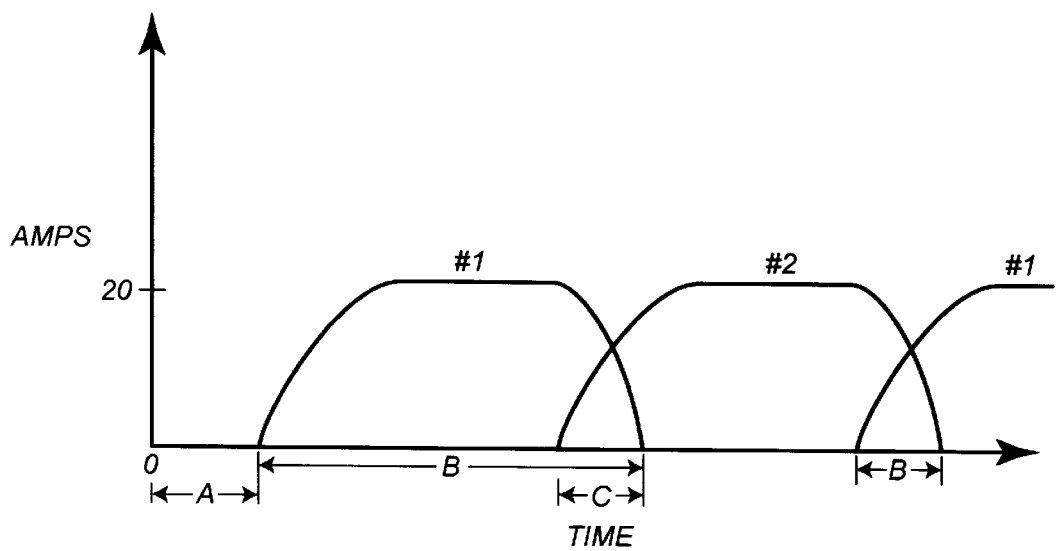
FIG. 6 is a graph showing the power draw associated with the operation of the present invention.
Figure 5:
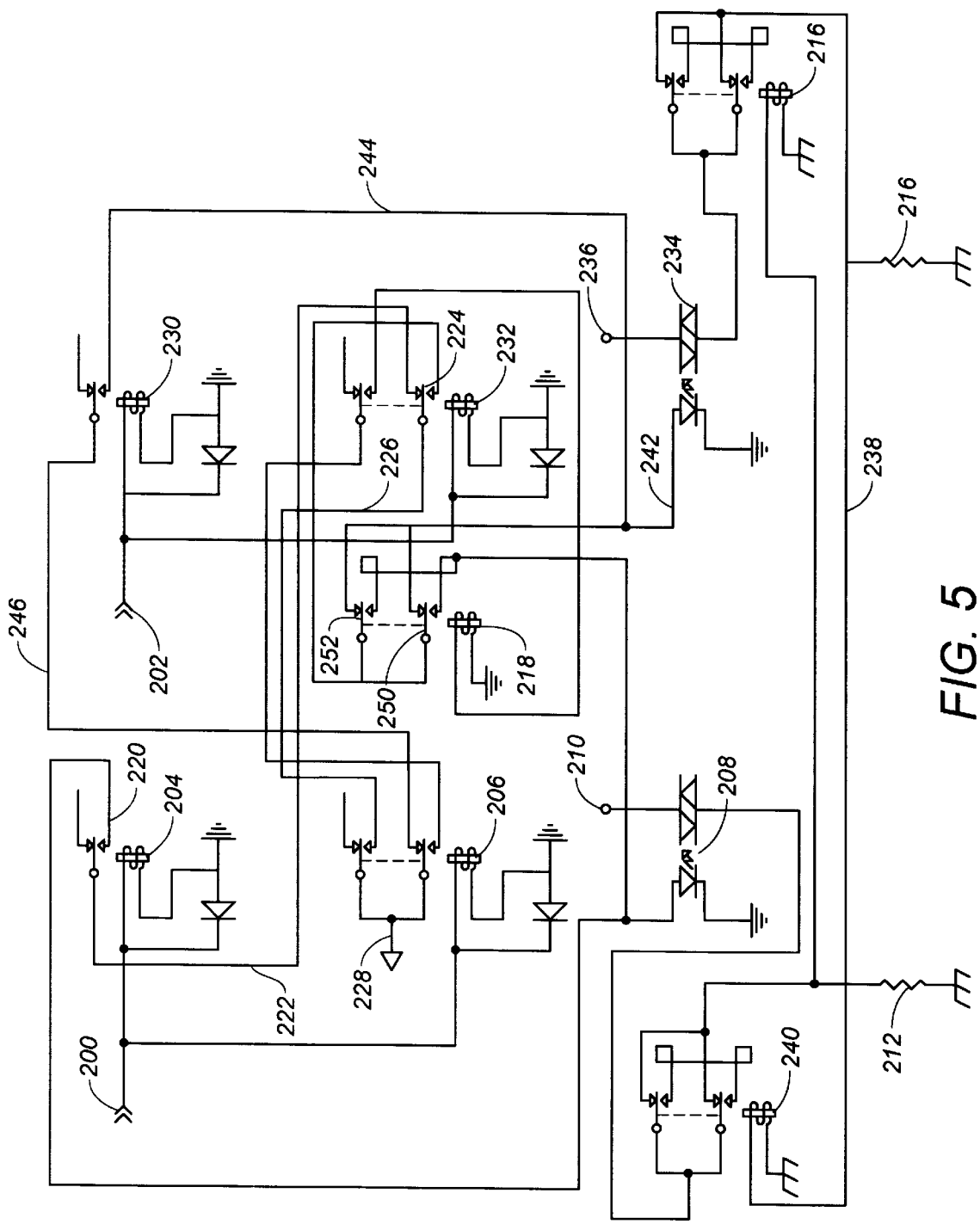
FIG. 5 is an electrical schematic of the heaters of the present invention.

FIG. 5 is a schematic of the electronics used in the present invention so as to prevent spikes or surges of power consumption. It is important to note that the present invention, in the heating mode, can heat the heat exchange liquid associated with the fluid flow lines during surgery for either one of the lines or both of the lines. The heating system can be in a condition whereby neither of the lines are to be heated, one of the lines are to be heated or both of the lines require heat. The operation of the present invention is relatively simple when neither of the lines require heat, or when a single line requires heat. However, the difficulty of the prior art occurs when both of the fluid flow lines during surgery require heat simultaneously. In the past, the operator would switch on the heating system associated with both of the fluid lines at the same time. The tremendous draw of power associated with the 1500 watt heaters cause an electrical surge or a current spike which could trip the circuit breakers or cause damage to auxiliary equipment. To avoid this problem, it was considered possible to switch one system on and the other system off simultaneously. However, experiments with this type of system indicated that spikes and power surges still occurred. It is believed the reason that such spikes and surges occurred would be that the heaters would continue to draw current even when deactivated. There is a declining draw of current after each of the heaters is deactivated. If the other heater is activated too quickly, then the other heater will be drawing current at full amperage while the other heater's consumption is declining. As a result, a momentary "spike" in current occurs. As such, for the electronics shown in the schematic of FIG. 5, it was found to be important to use relays so that the activation of one heater would be delayed a suitable time so that the consumption of energy remained at 20 amps or less cumulative by both of the heaters. FIG. 6 illustrates diagrammatically the intentions of the present invention. In FIG. 6, it can be seen that in interval "A", neither of the heaters is activated. Interval "B" shows the curve when the heater #1 is activated. The heater #1 will initially draw current until it reaches the peak amperage. When the heater #1 is deactivated, it will continue to draw power for a short period of time. This declining draw of power is shown by interval "C".

In the system of the present invention, the heater #2 can be activated immediately after the heater #1 is deactivated. As such, the startup power consumption will increase as the decrease in power consumption occurs by the heater #1 so that the total amperage remains constant at no more than 20 amps. This activating/deactivating interval is shown as interval "C". Since the cumulative amperage by heaters #1 and #2 remains constant at 20 amps, there will be no spikes or surges in power. The total power consumption will match system requirements. When heater #2 is deactivated, the power consumption will decline in the interval "D". At this time, the heater #1 can be activated so that the total power consumption remains at a cumulative 20 amps. The system, as shown by the schematic of FIG. 5, will switch heater #1 and heater #2 back and forth so as to continue to apply resistance heating to the heat exchange fluid. The fact that one heater is deactived at the time the other heater is active goes virtually unnoticed by the system. The transfer of heat to the heat exchange fluid will occur even though the respective heater is in an inactive state. The switching back and forth will cause a proper transfer of heat to the heat exchange fluid.

Referring to FIG. 5, heat controller inputs 200 and 202 are particularly shown. The heat controller inputs 200 and 202 provide a signal to the electronics of the present invention that either the heater #1 or the heater #2 requires activation.

When a signal is transmitted by heat controller 200, but not heat controller 202, the heater #1 will be activated. Initially, the signal is transmitted to the relay 204 and to the relay 206. Relay 204 will turn on the DC power supply so as to activate the solid state relay 208. The activation of the solid state relay 208 will allow the AC power supply 210 to activate resistance heater 212 for heating the heat exchange fluid. Similarly, the activation of the solid state relay 208 will transmit a signal to the relay 214 so as to prevent the activation of the second resistance heater 216. Since only one heater is on, as indicated by relay 204, the timer circuit 218 is bypassed. The current will pass along line 220, along line 222, by way of switch 224 and outwardly along line 226 as a control signal 228.

When the heat controller 202 is activated, but heat controller 200 is not activated, then the heat controller 202 will transmit a signal so as to activate relays 230 and 232. As a result, the solid state relay 234 will be activated so that the AC power supply 236 will pass to the second heater 216. Simultaneously, a control signal will be sent along 238 to the relay 240 so as to prevent activation of the heater 212. The relay 234 will cause a control signal to pass along lines 242, along line 244, along line 246 and to pass as a control signal at 228. The timer 218 is bypassed in this mode.

There are occasions when both the fluid lines require heating during the surgical procedure. In such a situation, both of the heat controllers 200 and 202 will provide a signal to turn on the respective relays 204 and 206 and 230 and 236. The logic of the system shown in FIG. 5 will cause the timer 218 to be activated. As a result, the timer will control the respective movement of the switches 250 and 252 so as to activate or deactivate the AC power supplies 210 and 236 from acting on the respective heaters 202 and 216. When the solid state relay 208 connects the power supply 218 to the heater 212, the relays will cause the power supply 236 to be disconnected from the heater 216. After a desired period of time, switches 250 and 252 will move to the alternate position whereby power is removed from the heater 212 and the solid state relay 234 will cause power from the AC power supply 236 to pass to the heater 216. The timer 218 will cause the power to alternate back and forth between the heaters 212 and 216.

Importantly, in the present invention, the use of such relays has been found to provide the necessary "delay" in the system so that instantaneous switching is avoided. This delay will cause one of the heaters to draw power at a declining rate while the other heater is drawing power at an increasing rate. Ideally, the heaters will decline and increase in power consumption at such a rate that the power spikes and power surges are avoided. So as to allow for proper heat to be passed to the heat exchange fluid, the timer can be set so as to switch back and forth between the heaters 212 and 216 approximately every four seconds.

It is important to note, in the present invention, that the AC power supplies 210 and 236 can be from a single source or from alternate sources. In the preferred embodiment of the present invention, since only a single plug is used for connecting the system 12 to a power supply, the AC power supplies 210 and 236 should preferably be the same power source.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A blood heating system for use in open heart surgery comprising:
    a first fluid circuit;
    a second fluid circuit defining a fluid flow pathway independent of said first fluid circuit;
    a first heater in heat exchange relationship with said first fluid circuit;
    a second heater in heat exchange relationship with said second fluid circuit;
    a power supply connected to said first and second heaters so as to supply a desired electrical power to said first and second heaters;
    a controller electrically interconnected to said power supply and to said first and second heaters such that said first and second heaters cannot be activated simultaneously; and
    a relay means electrically interconnected between said first and second heaters and said power supply, said relay means for deactivating one of said first and second heaters when the other of said first and second heaters is activated.

2. The system of claim 1, wherein each of said first and second heaters draw between 15 and 20 amps from said power supply.

3. The system of claim 2, wherein said timer means activates and deactivates said second heater after a desired period of time.

4. The system of claim 3, wherein said desired period of time is approximately four seconds.

5. The system of claim 1, said controller further comprising:
    a timer means connected to said relay means, said timer means for activating and deactivating said first heater after a desired period of time has passed.

6. The system of claim 1, wherein said power supply is a single 110 volt source of electrical energy.

7. The system of claim 1, wherein said relay means energizes one of said first and second heaters as the other of said first and second heaters is de-energized.

8. The system of claim 1, said relay means comprising:
    a first solid state relay interposed between said power supply and said first heater, said first solid state relay being switched by said controller so as to pass an alternating current from said power supply to said first heater; and
    a second solid state relay interposed between said power supply and said second heater, said second solid state relay being switched by said controller so as to pass the alternating current from said power supply to said second heater, said power supply being from a single electrical outlet.

9. The system of claim 8, said relay means further comprising:
    a first sensor interactive with said first fluid circuit adapted to sense a temperature of a fluid within said first fluid circuit, said first sensor being electrically connected to said first solid state relay so as to activate said first heater when the temperature of the fluid is below a desired level; and
    a second sensor interactive with said second fluid circuit adapted to sense a temperature of a fluid within said second fluid circuit, said second sensor being electrically connected to said second solid state relay so as to activate said second heater when the temperature of the fluid in said second fluid circuit is below a desired level.

10. The system of claim 9, said first sensor deactivating the first heater when the temperature of the fluid in the first fluid circuit is above a desired level, said second sensor deactivating said second heater when the temperature of the fluid in said second fluid circuit is above a desired level.

11. The system of claim 1, wherein each of said first and second heaters is a 1500 watt electrical heater.

12. A method of heating a first fluid circuit and a second fluid circuit in open heart surgery comprising:
    connecting a first heater in heat exchange relationship with the first fluid circuit;
    connecting a second heater in heat exchange relationship with the second fluid circuit;
    supplying electrical energy to the first and second heaters from a single power supply; and
    deactivating one of said first and second heaters when the other of the first and second heaters is activated such that the first and second heaters cannot be activated simultaneously.

13. The method of claim 12, said step of deactivating comprising:
    switching one of said first and second heaters to an activated state as the other of the first and second heaters is deactivated.

14. The method of claim 13, said step of switching comprising:
    switching said first and second heaters alternately between the activated state and the deactivated state after a desired period of time.

15. The method of claim 14, said desired period of time being approximately four seconds.

16. The method of claim 12, said step of supplying electrical energy comprising:
    supplying power to said first and second heaters such that said first and second heaters never draw more than 20 amps from said single power supply.

17. The method of claim 12, said step of deactivating comprising:
    connecting a first relay to said first heater; and
    connecting a second relay to said second heater, said first relay activating said first heater when said second relay deactivates said second heater.

18. The method of claim 12, further comprising:
    sensing a temperature of a fluid in said first fluid circuit;
    sensing a temperature of a fluid in said second fluid circuit;
    transmitting a signal to a relay connected to said first heater when the temperature of the fluid in said first fluid circuit is below a desired level;
    transmitting a signal to a relay connected to said second heater when the temperature of the fluid in said second fluid circuit is below a desired level;
    activating said first heater so as to elevate the temperature of the fluid in said first fluid circuit; and
    activating the second heater so as to elevate the temperature of the fluid in said second fluid circuit.

* * * * *